(12) United States Patent
Floeder et al.

(10) Patent No.: US 6,950,547 B2
(45) Date of Patent: Sep. 27, 2005

(54) WEB INSPECTION METHOD AND DEVICE

(75) Inventors: Steven P. Floeder, Shoreview, MN (US); James A. Masterman, Lake Elmo, MN (US); Matthew P. Peick, Eagan, MN (US); Carl J. Skeps, Lakeville, MN (US); Steven R. Wageman, St. Paul, MN (US); Wenyuan Xu, Oakdale, MN (US); Xi Yu, Woodbury, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 718 days.

(21) Appl. No.: 09/781,372

(22) Filed: Feb. 12, 2001

(65) Prior Publication Data

US 2002/0110269 A1 Aug. 15, 2002

(51) Int. Cl.[7] ............................................... G06K 9/00
(52) U.S. Cl. ...................... 382/143; 382/141; 382/144; 382/145
(58) Field of Search ........................ 382/141, 143–151, 382/134; 348/86, 87, 88, 126, 127, 128, 129, 125; 356/237.1, 238.1, 239.3, 237.5; 700/95; 435/39; 250/459.1

(56) References Cited

U.S. PATENT DOCUMENTS

| | | |
|---|---|---|
| 3,759,620 A | 9/1973 | Cushing et al. |
| 4,746,020 A | 5/1988 | Schenk |
| 4,752,897 A | 6/1988 | Zoller et al. |
| 4,776,023 A | 10/1988 | Hamada et al. |
| 5,305,392 A | 4/1994 | Longest, Jr. et al. |
| 5,365,596 A | 11/1994 | Dante et al. |
| 5,403,722 A * | 4/1995 | Floeder et al. ................ 435/39 |
| 5,434,629 A | 7/1995 | Pearson et al. |
| 5,440,648 A | 8/1995 | Roberts et al. |
| 5,774,177 A | 6/1998 | Lane |
| 6,014,209 A * | 1/2000 | Bishop .................... 356/237.5 |
| 6,031,931 A | 2/2000 | Chiu et al. |
| 6,252,237 B1 * | 6/2001 | Ramthun et al. ........ 250/459.1 |
| 6,259,109 B1 | 7/2001 | Dalmia et al. |
| 6,330,350 B1 * | 12/2001 | Ahn et al. .................. 382/134 |

FOREIGN PATENT DOCUMENTS

| | | |
|---|---|---|
| EP | 0 681 183 A2 | 11/1995 |
| EP | 0 898 163 A1 | 2/1999 |
| EP | 1 022 906 | 7/2000 |
| WO | WO 99/10833 | 3/1999 |
| WO | WO 00/07031 | 2/2000 |
| WO | WO 01/02840 | 1/2001 |

OTHER PUBLICATIONS

"A PC–Based Real Time Defect Imaging System for High Speed Web Inspection", by J.W. Roberts, S.D. Rose, G. Jullien, L. Nichols, G. Moroscher, P.T. Jenkins, S.G. Chamberlain, R. Mantha, and D.J. Litwiller, pp. 7–29–7–41.

(Continued)

*Primary Examiner*—Vikkram Bali
(74) *Attorney, Agent, or Firm*—Brian E. Szymanski

(57) ABSTRACT

An imaging device for sequentially imaging a portion of a continuously moving web to provide a digital data stream which is then analyzed by a single computer without the used of dedicated signal processing hardware. Techniques for operating on the data stream from an imaging device are disclosed, particularly including operations based on blob information stored in terms of starting position and segment run lengths in a crossweb direction. These allow definitions of blobs to be accumulated in a line-by-line fashion, and allow classes of defects commonly found in continuous web manufacturing to be identified with far less computing power than was previously required. In particular, in the challenging application of inspecting flexible circuits, data rates in excess of 10 mega-pixels/second are achieved and successfully processed.

47 Claims, 7 Drawing Sheets

OTHER PUBLICATIONS

"Real–Time Computer Vision on PC–Cluster and Its Application to Real–Time Motion Capture", by Daisaku Arita, Satoshi Yonemoto, and Rin–ichiro Taniguchi, pp. 205–206.

Technical Paper "The Application of a Flexible Machine Vision Architecture to the Inspection of Continuous Process Materials", by Brad Harkavy, from a conference attended on Apr. 24–27, 1989.

"Flexible Circuits Roll–to–Roll AOI" by Brian Tithecott, pp. 26–32.

"A New Design Environment for Defect Detection In Web Inspection Systems", by S. Hossain Hajimowlana, Roberto Musceder, Graham A. Jullien, James W. Roberts; pp. 125–136.

"Parsytec HTS–2, Defect Detection and Classification Through Software vs. Dedicated Hardware", by Reinhard Rinn, Scott A. Thompson, Dr. Ralph Foehr, Friedrich Luecking, and John Torre, Jan. 1999, pp. 110–121.

* cited by examiner

WEB INSPECTION METHOD AND DEVICE

FIELD OF THE INVENTION

The present invention relates to automated inspection systems, and more particularly to a system and device for optically inspecting continuously moving webs.

BACKGROUND OF THE INVENTION

Inspection systems for the analysis of moving web materials have proven critical to modern manufacturing operations. Industries as varying as metal fabrication, paper, non-wovens, and films rely on these inspection systems for both product certification and online process monitoring. Equivalent verification of product quality is much more expensive if performed off-line or manually after fabrication of the web materials.

A difficult factor in the design of all such inspection systems is the high rate of data acquisition and processing. Conventional commercial web manufacturing operations utilize web dimensions and web speeds requiring inspection data acquisition rates of tens or even hundreds of mega-pixels per second. Furthermore, these data rates are provided in a continuous manner in order to fully scan the moving web. The noted data rates are considered extensive and have resulted in the development of custom image processing engines to address the large continuous data rates.

The art has responded to this dilemma by using dedicated electronic hardware to preprocess the data stream, generally utilizing multiple paths and multiple layers of dedicated modules. Such a system is capable of sustaining the data rates required for the inspection of moving webs. However, there are difficulties related to the necessary customization of both hardware and software required for the dedicated preprocessors. These inspection systems are highly custom, thus limiting the range of applications possible with a given system. For example, a system developed for inspecting metals will not be able to also inspect printed packaging. Because of this customization, dedicated electronic hardware also require high development costs in both money and time, they are relegated to performing only simple image processing operations in real time, and they have limited future expansion and correspondingly high maintenance costs.

The manufacturing industry has recognized the importance of flexibility in its operations. Achieving this goal often has manufacturers working to develop systems and devices that allow a rapid change over between various products. Unfortunately, while web inspection systems have proven valuable and even indispensable for some industries, they have not been successful in addressing the increased pace of change in manufacturing. Specialized signal processing hardware does not permit the rapid change over between various products that optical inspection of moving webs now requires. It would be desirable to be able to perform all the required processing on a single general-purpose computer, so that change over between product lines could be accomplished by merely loading the required software. Additionally, it would also be desirable to reduce the development time and cost associated with custom hardware systems. So far, that end has not been possible.

SUMMARY OF THE INVENTION

The present invention provides a system capable of inspecting moving webs even at high data rates. The discovery of new methods of analysis has brought the difficulty of online optical inspection within the range of commercially available general-purpose computing power. With an inspection system according to the present invention, many different products can be inspected by the same hardware, needing only the loading of product specific software which contains the information about what constitutes a defect in that product.

The device of the present invention includes an imaging device for sequentially imaging a portion of a continuously moving web to provide a digital data stream. The stream represents sequential portions of the web rather than an area image such as is used conventionally in machine vision techniques. A single computer is used to analyze the digital data stream. The single computer first forms a blob list from the digital data stream and uses inventive algorithms to identify defects on the continuously moving web. High web speeds and complicated patterns on the web may be handled through the present invention. In particular, the present invention is well adapted to the challenging application of inspecting flexible circuits, and data rates in excess of 10 mega-pixels/second are achieved and successfully processed.

Alternatively, the invention includes a method of continuously inspecting a moving web. The method involves imaging a sequential portion of the web to provide a digital data stream. A single computer then processes the digital data stream by first forming a blob list from the data stream and then analyzing the blob list to identify defects on the continuously moving web. Optionally, the data stream may be filtered prior to the formation of the blob list in order to improve the image for analysis.

For purposes of the present invention, the following terms used in this application are defined as follows:

"web" means a sheet of material having a fixed dimension in one direction and indeterminate length in the orthogonal direction;

"sequential" means that an image is formed by a succession of single lines, or areas of the continuously moving web that optically maps to a single row of sensor elements (pixels);

"single computer" means a general purpose computer having two principal characteristics: 1) the ability to respond to a specific set of instructions; 2) the ability to execute a prerecorded list of instructions;

"pixel" means a picture element represented by one or more digital values;

"blob" means a connected set of pixels in a binary image;

"defect" means an undesirable occurrence in a product;

"gray scale" means pixels having a multitude of possible values eg 256 digital values;

"binarization" is an operation for transforming a pixel into a binary value;

"filter" is a mathematical transformation of an input image to a desired output image, filters are typically used to enhance contrast of a desired property within an image; and "covercoat defect" means an insufficient or extraneous coating on a web.

Other features and advantages will be apparent from the following description of the embodiments thereof, and from the claims.

BRIEF DESCRIPTION OF THE DRAWINGS

The above, as well as other advantages of the present invention will become readily apparent to those skilled in the art from the following detailed description when considered in the light of the accompanying drawings in which.

DETAILED DESCRIPTION

Figure 1:
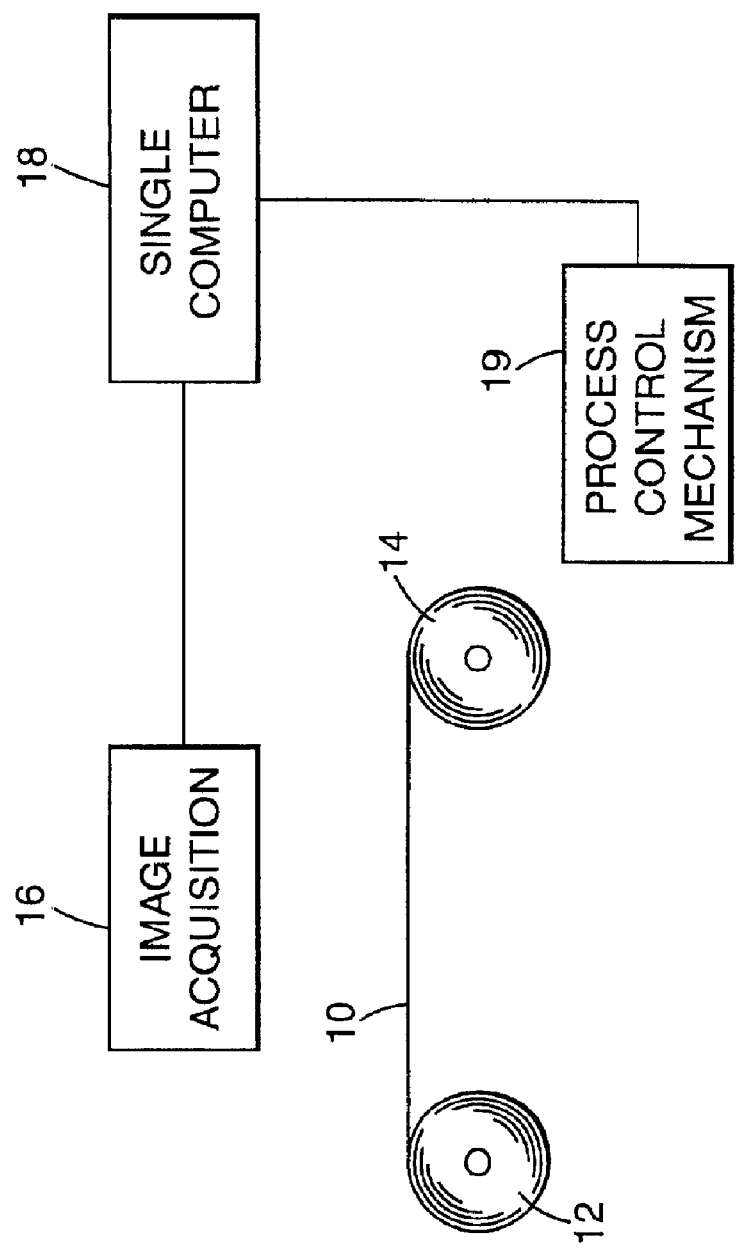
FIG. 1 is a block diagram demonstrating the method of the present invention.

The present invention is a method for optically inspecting a continuous moving web. FIG. 1 is a diagram depicting the method of the present invention. A segment of a continuously moving web 10 is positioned between two support rolls 12, 14. An image acquisition device 16 is positioned in close proximity to the continuously moving web 10. The image acquisition device scans a sequential portion of the continuously moving web 10 to obtain data about the respective sequential portion. The data is transmitted to a single computer 18 that collects and analyzes the data to determine the presence of defects on the web 10. The resulting determination may then be optionally sent to a process control mechanism 19 for execution of additional process commands.

Web Materials

In accordance with the present invention, the continuously moving web may include any sheet-like material that has a predetermined width and thickness and an indeterminate length. Materials provided in web form that may be optically imaged are suitable for use with the present invention. Examples of web materials include, but are not limited to, metals, paper, wovens, non-wovens, glass, polymeric films or combinations thereof. Metals may include such materials as steel or aluminum. Wovens generally include various fabrics. Non-wovens include materials, such as paper, filter media, or insulating material. Films include, for example, clear and opaque polymeric films including laminates and coated films.

One type of inspection problem particularly suitable to resolution through use of the present invention is the inspection of optical films. A second type of inspection problem is the inspection of flexible circuit webs. The invention is particularly suited for dealing with the complexity involved where individual circuits on a flexible circuit web have repeating circuit patterns deposited or formed on a flexible substrate. A web typically has multiple individual circuits each including various small parts arranged in arbitrary patterns. The individual circuits are later separated from the web by e.g. die cutting for use in discrete electrical applications.

For many applications suited for the present invention, the web materials or combined materials may preferably have an applied coating. Coatings that may be optically imaged are suitable for use with the present invention. The coatings are generally applied to an exposed surface of the base web material. Examples of coatings include adhesives, optical density coatings, low adhesion backside coatings, metalized coatings, optically active coatings, electrically conductive or nonconductive coatings, or combinations thereof. The coating may be applied to at least a portion of the web material or may fully cover a surface of the base web material.

Method for Inspecting a Web

Figure 2:
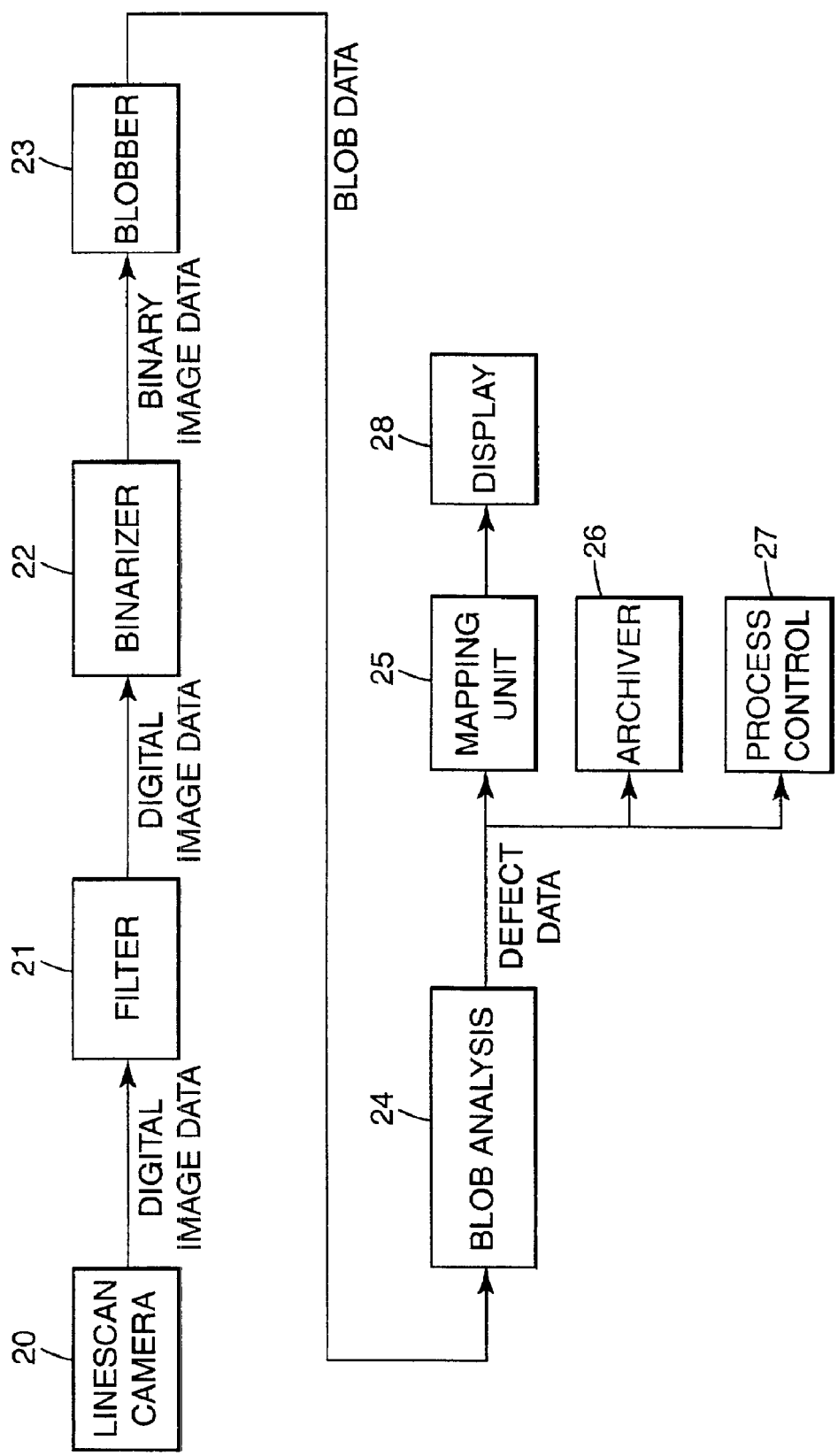
FIG. 2 is a detailed block flow diagram of the image acquisition and image processing elements of the present invention.

The method of the present invention utilizes an image acquisition device to acquire a detailed image of a sequential portion of a continuously moving web. The resulting image is preferably provided in a data stream of at least 10 mega-pixels per second. The data stream is sent to a single computer where it is formed into a blob list. The single computer then analyzes the blob list to determine defects. FIG. 2 illustrates the method of the present invention. The first step 20 involves the acquisition of image data from a surface of a continuously moving web. The data, prior to formation of a blob list in step 23, may optionally be filtered 21 and binarized 22. The blob list, upon formation, is then processed in step 24 wherein the analysis occurs to identify defects on the continuously moving web. The output from step 24 is optionally sent to one or more of the following: a mapping unit 25, an archiving database 26, an operator display 28, or a process controller 27.

Image Acquisition

The image acquisition is accomplished through the use of conventional imaging devices that are capable of reading a sequential portion of the moving web and providing output in the form of a digital data stream. For purposes of the invention, the imaging device may include a camera that directly provides a digital data stream or an analog camera with an additional analog to digital converter. Furthermore, other sensors, such as for example, laser scanners may be utilized as the imaging device. A sequential portion of the web indicates that the data is acquired by a succession of single lines. Single lines comprise an area of the continuously moving web that optically map to a single row of sensor elements or pixels. Examples of devices suitable for acquiring the image include linescan cameras such as Model#LD21 from Perkin Elmer (Sunnyvale, Calif.), Piranha Models from Dalsa (Waterloo, Ontario, Canada), or Model#TH78H15 from Thompson-CSF (Totawa, N.J.). Additional examples include laser scanners from Surface Inspection Systems GmbH (Munich, Germany) in conjunction with an analog to digital converter.

Figure 3:
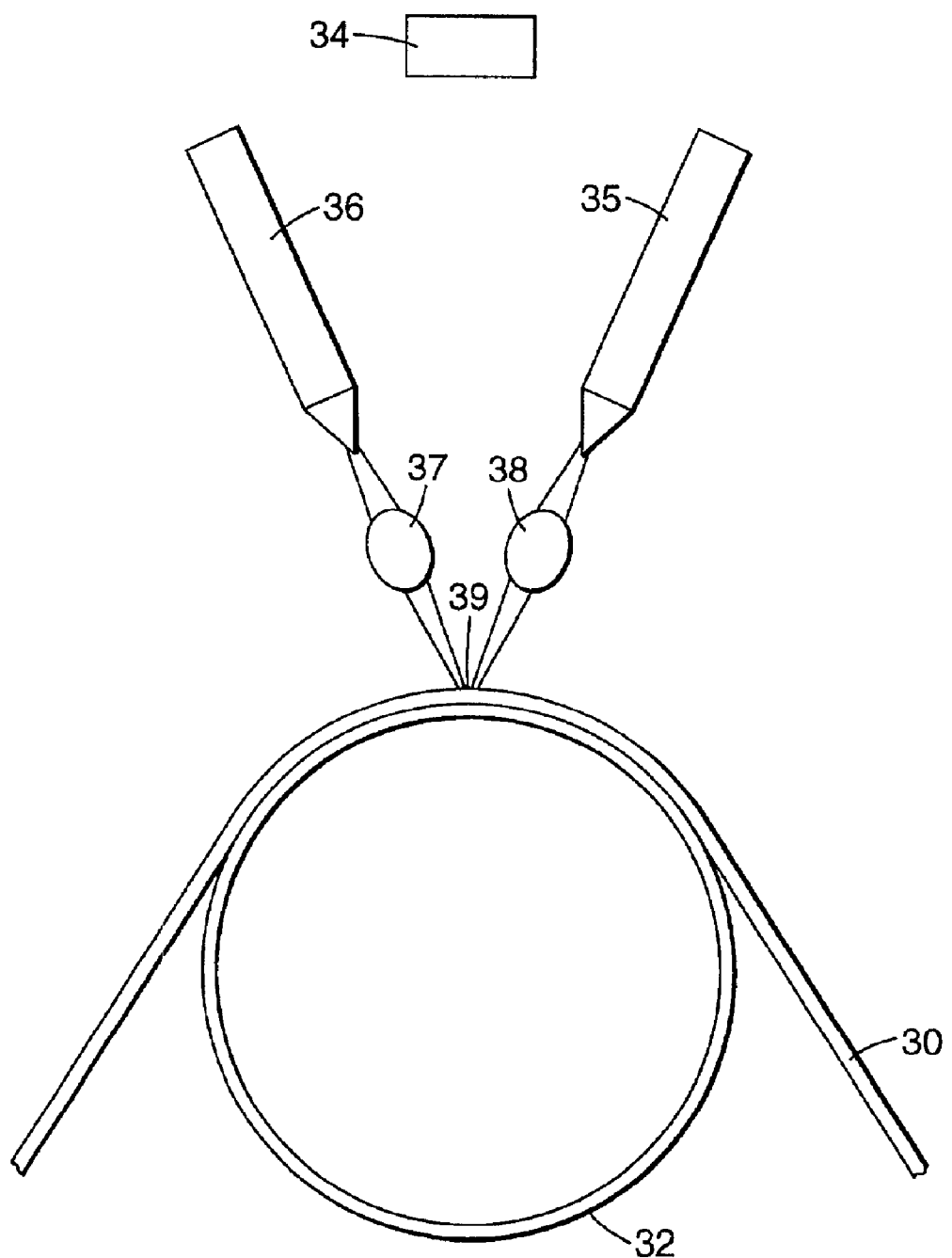
FIG. 3 is an example of an optical lighting assembly utilizing reflected light.

The image may be optionally acquired through the utilization of optic assemblies that assist in the procurement of the image. The assemblies may be either part of a camera, or may be separate from the camera. Optic assemblies utilize reflected light, transmitted light, or transflected light during the imaging process. Reflected light is suitable for the detection of defects caused by web surface deformations such as surface scratches. FIG. 3 illustrates the use of reflected light for image acquisition on a continuously moving web 30. A web 30 traveling on an idler roll 32 passes over a image acquisition device 34. Fiber optic lights 35, 36 direct light through cylindrical focussing lenses 37, 38 at a focal point 39 common with the that of the image acquisition device 34. Conventional fiber optic lights and focussing lenses are suitable for use in the present invention.

Figure 4:
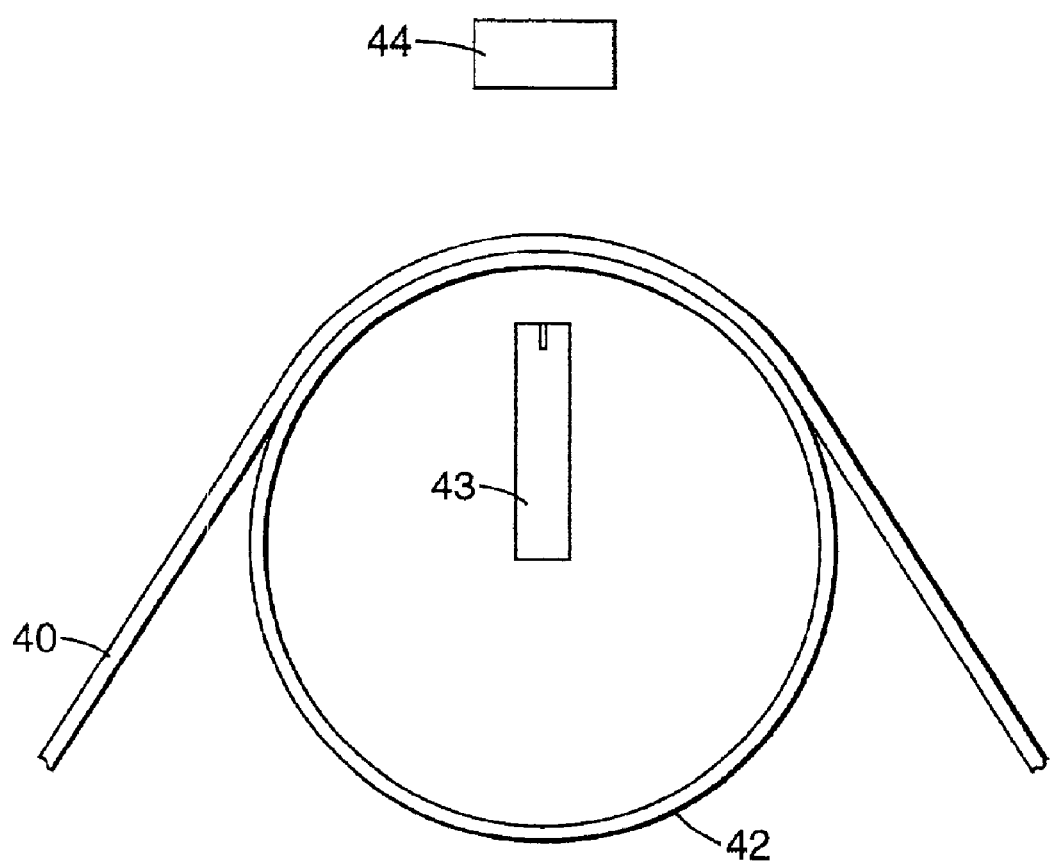
FIG. 4 is an example of an optical lighting assembly utilizing transmitted light.

Transmitted lighting is used for the detection of defects that disturb normal transmission of the light as it passes through the web, such as gels in extruded films or optical density variations in coated films. FIG. 4 depicts the utilization of transmitted light through a glass idler roll 42 and a corresponding web 40 traveling on the glass idler roll 42. In operation, light is transmitted from the fiber optic light 43 through the glass idler roll 42 and through the web 40. The image acquisition device 44 is positioned above the focal area of the transmitted light.

Figure 5:
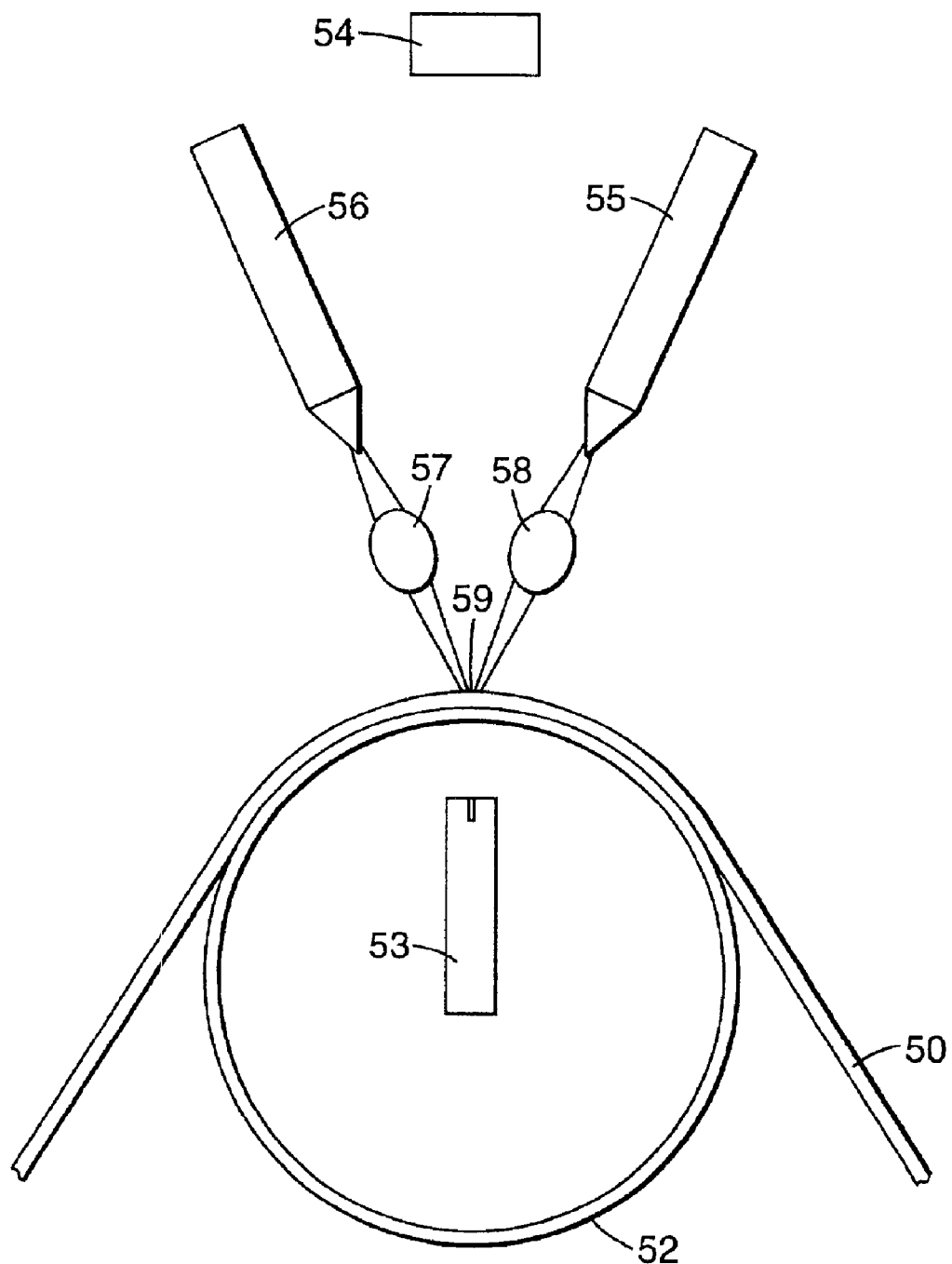
FIG. 5 is an example of an optical lighting assembly utilizing transflected light.

Transflected lighting is a combination of both reflected light and transmitted light that is most preferred for detecting hybrid defects such as covercoat continuity on flexible circuit webs. An example of transflected lighting is depicted in FIG. 5. A web 50 is conveyed over a glass idler roll 52. Fiber optic lights 55, 56 direct light through cylindrical focussing lenses 57, 58 at a focal point 59 common with the that of the image acquisition device 54. Light is also transmitted from the fiber optic light 53 through the glass idler roll 52 and through the web 50. The focal point for the transmitted light coincides with the focal point from the reflected light sources 55, 56.

Figure 6A:
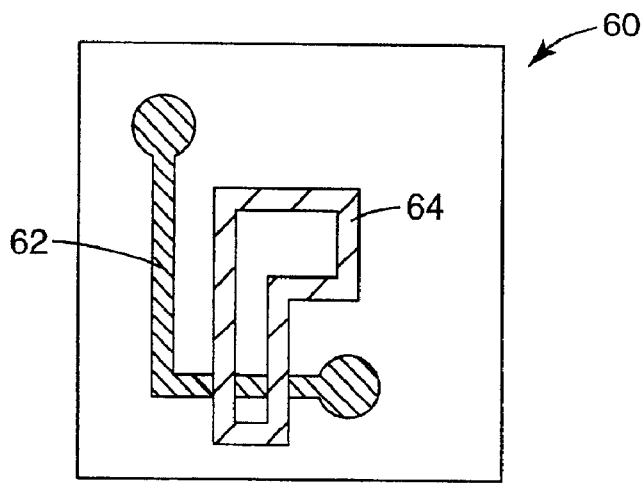
FIGS. 6a, 6b and 6c are examples of the way a representative patterned web might appear when utilizing reflected light, transmitted light, and transfected light, respectively.
Figure 6B:
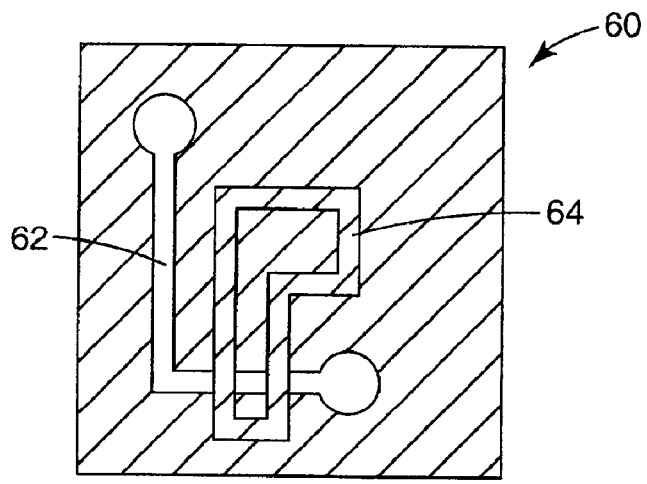
Figure 6C:
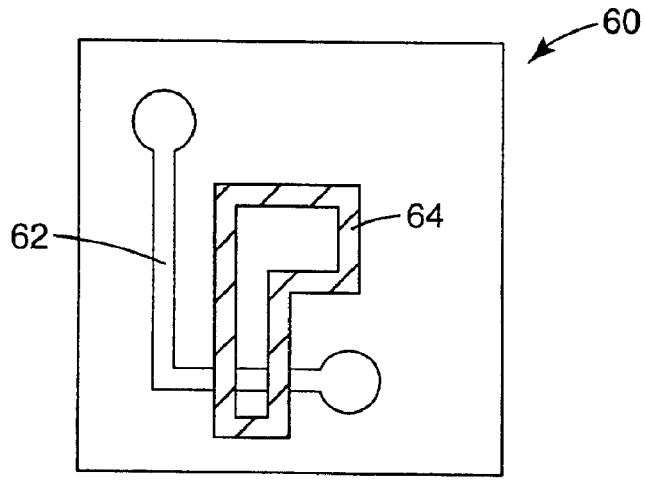

In a preferred embodiment for the inspection of flexible circuits, all three optical configurations may be utilized. FIGS. 6a, 6b and 6c demonstrate the potential uses of the lighting configurations when applied to a flexible circuit web. Transmitted light is used for the detection of defects on the flexible circuit web such as substrate holes that appear as bright spots on a dark background. It can also be used for detection of electrical continuity defects such as shorts and opens. FIG. 6a illustrates how such defects may be detected utilizing transmitted light. According to FIG. 6a with transmitted light, the metal circuit elements 62 and non-conducting covercoat 64 appear dark with the substrate 60 appearing light. This has the advantage that the widest representation of the circuit trace is imaged such that edge sloping due to the circuit etching process causes no difficulties. Reflected light, as shown in FIG. 6b, can be used for circuitization defects if desired, but is required for the detection of surface finish defects, such as stains on the bonding pads, that may cause failures in later processing steps. In these cases, the metal circuit elements 62 and the non-conducting covercoat 64 appear bright with defects obscuring the light. Transflected light, or a combination of both reflected and transmitted lighting, provides a substantially different analysis for the detection of circuit coating such as solder dams of dielectric covercoats that span both metal and substrate features. In these cases, sole use of either reflected or transmitted light is inadequate because of the drastically different properties of the metal compared to the substrate. However, by using transflected lighting, the coating can be easily distinguished from both the metal and substrate features. FIG. 6c demonstrate the concept of transflected light in which element 62 has an image different than that of element 64.

Filtering, Binarization, and Blobbing

The digital data stream is transmitted from the imaging device to the processing computer. Inspecting webs is a very demanding application because the data is continuous; as long as the web is moving, data is flowing to the system. Thus, the processing computer must have the capability of sustaining the required processing rates indefinitely. The method of the present invention is capable of handling data rates for continuously moving webs preferably from about 10 mega-pixels/second or greater and most preferably about 30 mega-pixels/second or greater, depending on the specific application requirements.

In one preferred embodiment relating to a uniform film product, the web speed is 600 ft/min, the web width is 50 inches, and the imaging resolution is 20 mils/pixel. The required sustained data throughput is approximately 15 mega-pixels/second. In a second embodiment related to flexible circuit inspection, the web speed is 25 mm/second, the web width is 70 mm, and the imaging resolution is 10 $\mu$m/pixel. The required sustained data throughput is then approximately 17.5 mega-pixels/second.

The digital data stream is sent to a single computer for analysis. In accordance with the present invention, a single computer, as previously noted, is a general purpose computer having two principal characteristics: 1) the ability to respond to a specific set of instructions; 2) the ability to execute a prerecorded list of instructions. For purposes of the invention, all general purpose computers having memory components, mass storage components, a central processing unit, and optionally input and output devices are suitable for use with the present invention. The present invention specifically excludes such devices as digital signal processors and other limited computer processing boards designed explicitly for high speed execution of mathematical operations. Most preferably, "single computer" includes single mother board, general purpose microcomputers.

Optionally, prior to formation of the blob list, it may be desirable to filter the incoming digital data stream to enhance the contrast of a desired property within the image. For example, filters are often utilized to reduce noise or increase the contrast of features, such as edges. In general, filters may include separable filters, linear filters, non-linear filters, local contrast enhancement filters, edge enhancement filters, noise reduction filters, or combinations thereof. The formation and use of the noted filters are conventionally recognized by those skilled in the art. In the present invention, the parameters of these filters and mappings are determined by randomly sampling pixels rather than that entire image. Also, these operations are executed only in the region of interest A separable filter may also be utilized in conjunction with the present invention. Filters in image processing are generally two-dimensional. However, most of them can be carried out or approximated by executing a vertical one-dimensional filter and a horizontal one-dimensional filter in proper order. Thus, the computational cost has been reduced from $O(n^2)$ to $O(2n)$. For example, a vertical filter is used to remove the cross web non-uniformity resulting from the non-uniformity of the optical field and sensors. Then, a horizontal smoothing filter may be used to reduce the high-frequency random noise.

Another step executed in the single computer prior to formation of the blob list involves binarization. Binarization is the transformation of images with pixels having a multitude of values such as color or grey scale images into binary images.

One form of binarization is fixed binarizing. Fixed binarizing is based on a single level throughout the image. For example, when binarizing at a value 128, all pixels with values greater than 128 are transformed to the value "1" (white) while those less than or equal to 128 are transformed to "0" black. The image may then be blobbed according to the blobbing procedures of the present invention.

Another form of binarization is adaptive binarizing. Adaptive binarizing is based on dynamic analysis of the image. The threshold value for each pixel is determined through the analysis of other pixels in the image such that different pixels will have different threshold values. This compensates for low contrast or intensity varying images. There are a variety of methods for performing this operation.

For example, the threshold value for a pixel could be calculated by averaging the 20 closest neighbor pixels. If the image were twice as bright on the left as the right, a fixed threshold value for binarization would cause significant variations in the detection probability depending on the exact defect location. However, when using adaptive binarization, a local upset would be equally detectable on the left side as on the right. This approach is able to compensate for reasonable background intensity variations.

For the preferred embodiment with unpatterned polymeric films, the threshold used for binarization is conveniently computed using localized intensity analysis averaging within a neighborhood. When the web is a patterned web, and particularly when flexible circuit webs are inspected, a particular mode of adaptive thresholding prior to the binarizing of the pixels in the data stream has been found as preferred. This involves identifying at least one sequential portion of the web having substantially the entire range of optical properties characteristic of the web. The line within the repeating pattern that contains as many different visual features as possible is considered the optimum choice. Particular note is taken of the data stream corresponding to that line, identifying the pixel values corresponding to local maxima and minima. A range of pixel values is defined bounded by the lowest value among the pixel values identified as local maxima and the highest value among the pixel values identified as local minima. Then a threshold value is calculated within the range according to some appropriate rule; for flexible circuits, a calculated threshold value equal to [lower bound+0.75×(upper bound—lower bound)] has yielded good results. At least a portion of the digital data stream, conveniently the portion until the next time the identified line appears in the repeating pattern, is binarized using the calculated threshold value.

Depending on the defects to be analyzed, it may be desirable to use multiple threshold values for binarization with each value for a specific defect type. For example, in a preferred embodiment for the inspection of flexible circuits using transmitted lighting, the metalized features appear dark in reference to the substrate. By using a higher threshold value for detection of shorts and a lower threshold value for the detection of opens, one can significantly increase detection probability.

In accordance with the present invention, the single computer executes at least both the formation of a blob list and the analysis of the blob list to determine defects on the continuously moving web. A blob is a connected set of pixels in a binary image. A connected set of pixels generally indicates that the pixels are either 4-connected (four neighbors: above, right, below, left) or 8-connected (eight neighbors: above, upper right diagonal, right, lower right diagonal, below, lower left diagonal, left, upper left diagonal). A blob list is formed in the following manner. First, a binarized image is presented to the blobbing mechanism with a foreground value and connection scheme. The foreground value represents the value of the pixels of interest in the image. This value is either the binary minimum (typically 0) or the binary maximum (typically 255). The connection scheme is specified as either four connected or eight connected respectively.

Regardless of the blob connection scheme being used, the presence of a blob is associated with the connection of pixels. As each sequential portion of the web is scanned, the digital data stream corresponding to that sequential portion describes pixels in an X domain corresponding to their position across the web. For each line, collections of pixels connected to each other in the X domain are defined as segments. Once these segments are defined in the X domain for a line, it becomes possible to resolve, in a line by line fashion, if those pixels are connected in the Y domain. The Y domain corresponds to the direction of web movement. For computational convenience, a segment can be represented as a collection of information pertaining to the segment that uniquely identifies it in the image. Representing a segment in terms of starting position in the X and Y domains, and run length in pixels in the X domain, has proven particularly convenient.

Through the compilation and use of this information, the blobbing process can be reduced to a formation of X segments for each line and a resolution of the connections of the X segments from line to line. For computational efficiency, the present invention preferably completes both the formation of a list of X segments and conversion of the list into a blob list in a single iteration. The present invention's single iteration algorithm only requires saving a list of the X segments from the previous line as a comparison list. The existence of connections between the list of segments in the current row and the segments in the comparison list is resolved line by line accumulating the information that will define blobs.

The process starts at the first line in the Y domain and iterates over each subsequent line. A running count of open segments for each blob is maintained throughout the process. This serves to automatically account for the addition of new blobs, the closing of completed blobs, and the merging of separate blobs into a single blob such as at the base of a letter "V". The invention determines the first segment in the current line as referenced from the minimum X position. If that X segment's end position is less than the start position of the current segment in the comparison list, the segment must be the first segment in a new blob. At this point, a new blob is allocated, the open segment count for that blob is incremented, and the segment is assigned as the first segment in this blob. If the end of the corresponding segment in the comparison list is less than the start position of the current segment, the corresponding segment in the comparison list is removed from the comparison list, the open segment list is decremented, and the comparison begins again. However, if neither of these cases is satisfied, the current segment and the corresponding segment in the comparison list must overlap and be part of the same blob. The segment is added to developing blob encompassing the segment from the comparison list. If multiple current segments overlap a single segment from the comparison list, then they are added to the current developing blob. Also, if the current segment overlaps multiple segments, N, from the comparison list, then a merge condition exists. The individual developing blobs represented by segments on the comparison list are combined into a single blob and the open segment list is decremented by N−1. Finally, if there is no segment in the current line contiguous with a segment in the comparison list, then the open segment count is decremented for each segment in the comparison list.

Since the physical web has indeterminate length, the blobbing process may continue indefinitely. However, individual blobs are deemed complete when their open segment count is zero, at which point they are available for further analysis.

Web Synchronization

The web inspection system of the present invention is generally synchronized to the continuously moving web in order to retain spatial registration. The present invention preferably utilizes an analysis coordinate system that corresponds to a physical web position registered to the video data and analysis stream. With conventional optical inspection systems this is usually accomplished using a rotary encoder physically attached to the web line. Rotary encoders may include, for example, model#ROD523 from Heidenhain, Traunreut, Germany. As the web moves, the encoder outputs a succession of digital signals at regular distance intervals. Often, each pulse from the encoder is used to trigger the camera to image another line across the web.

A preferred method involved for synchronizing flexible circuit webs utilizes a technique for locating a likeness of a subset of data in a relatively large sample. Mathematically, the best way to determine the likeness of one data set to another is to create a correlation coefficient that describes numerically the relationship between two data sets. Although there are many methods for achieving this correlation coefficient, they are generally computationally expensive and not feasible for use in real time. However, the present invention first reduced the data sets to a binary result, upon which adequate processing speeds can be achieved.

With the preferred embodiment of flexible circuit webs, the web generally contains a succession of individual circuit parts that will later be excised and attached to active circuit elements. During manufacturing, these parts may be oriented spatially on the web in many different forms including but not limited to N×M arrays, single parts that span the entire web, and interwoven parts rotated 180 degrees from their nearest neighbor. However, the one constant in this process is that spatial orientation of the circuits will always follow a clear and deterministic pattern in the down web direction. The present invention uniquely identifies and segments discrete parts regardless of the number or orientation of the parts across the web based solely on the information contained in the incoming video stream with no need of external sensors or external synchronization mechanisms.

The preferred binary correlation operates by first acquiring a predefined correlation image. This may be loaded from a file, or other data storage mechanism. Next, the predefined correlation image is binarized with a predefined threshold. Once the correlation image has been binarized, an additional under sampled image having reduced resolution is created from the original binarized correlation image. The under sampled image is used to speed the correlation process. The original image can be under sampled to any degree. However, powers of two are preferred for ease of computations. After the locating image has been binarized and under sampled it is stored in RAM for repeated use in correlation.

At this point, an arbitrary image can be presented to the location mechanism for correlation. Every arbitrary image is presented with a binarization threshold, a search acceptance variable, and a search certainty variable. The search acceptance variable is used as a measurement of the minimum acceptable correlation that will be considered a match. The search certainty variable is used for speed purposes and tells the location mechanism that it can stop searching immediately if it finds a correlation greater than or equal to it.

Before location can begin, the arbitrary image may also be binarized and sub sampled to the same degree as the original location image. The arbitrary image is binarized using the threshold value supplied to the location mechanism as previously described. The binarization value need not be the same as the value supplied with the locating image. This allows for changes in lighting and sensitivity of the acquisition device.

Once the preparatory work has been completed, location can commence. The location correlation amounts to a pixel by pixel subtraction between the original pattern and a sub section of the larger arbitrary image. The correlation coefficient is determined by summing the result of the subtraction. A result of zero constitutes a one hundred percent certainty of match, where a result of [width×height×binary maximum] (typically 1 or 255) represents no match at all.

The correlation is done first on the under sampled images and a general location and certainty of this location is determined. Since the results of the under sampled correlation inherently yield a location of plus or minus n−1 pixels (where n is amount of the under sample), a second correlation is done on the original images in order to further restrict the location of the under sampled correlation to an even greater degree. Finally, when this process is complete, the exact location of the match, if any, is communicated to the interested party and the location mechanism is ready to continue correlation on other arbitrary images.

With an adequate location mechanism in place, the invention can proceed with the process of locating and extracting parts solely from the digital data stream. To achieve this end, the invention uses several predefined digital images as correlating patterns. These digital images, or locators, include a method to determine the location of the web in the X and Y domain of the digital data stream as well as a method to determine the exact location of each discrete part within the coordinate system of the web. Furthermore, locators may be used to locate distinct regions of interest within the coordinate system of the part itself.

The first step in this process is to identify the exact position of the web in the digital data stream. The exact position is determined using a binary correlation of a predefined web locator image and the sequential digital data stream. Since the predefined web locator contains a pattern that occurs only once in the down web distance between repeating patterns, this correlation serves to establish the origin of the X and Y coordinate system of the web.

With the web locator's position being known, the invention can establish the exact cross and down web position of each part that occurs in an instance of the down web repeating pattern. Once again, this is accomplished using the binary correlation of a predefined part locator image and the sequential digital data stream. However, to conserve computational cycles, this operation is performed in a limited crossweb location as determined by the offset of part locator from the web locator and the actual width of part locator.

Since the number of parts and their offsets from the web locator are predetermined, an accurate location mechanism as described above can achieve near perfect accuracy in finding all parts on the web. Furthermore, it stands to reason, that if a discrete part can be located, excised digitally, and then optionally masked and rotated to a single orientation, all additional processing can be done without respect for the original orientation and cross web location.

The processing pipeline will preferably operate on individual parts. Therefore, all the detection algorithms work identically, regardless of web patterns, number of parts across the web, etc. If a product changes, the operator need only select the new product from a menu. If an upset such as a splice occurs, it will detect the upset and resynchronize itself automatically because it bases all its object recognition on only the video stream. Also, because a predefined part locator is used this method automatically and continually corrects for crossweb wander and other effects inherent to web processes.

Defect Analysis

Web inspection applications can generally be divided into two distinct classes, patterned (such as labels, currency, and flexible circuits) and unpatterned (such as films and nonwovens). This invention is capable of successfully performing either type of application without any inspection hardware change. By changing software to perform different types of blob analysis, the generic single-based computer system can accomplish a wide variety of applications.

For unpatterned webs, the video signal is expected to be uniform so that any nonuniform areas are defective. Video processing to identify defects entails filtering to enhance the nonuniform video signals, binarization to separate defective areas from the background, and blobbing to collect defective pixels into unified entities as previously described. Finally, the collected blobs are analyzed to determine if they represent defective portions of the web or just anomalies that are not defective. The classification consists of analysis of the blob position and geometric shape parameters. If a particular blob has features consistent with predefined defects, then it is defective. However, if it is not within the tolerances of predefined defects, then it is not defective. Methods of defining or training the system to recognize defects are described below.

For example, in a preferred embodiment for the inspection of translucent polymeric webs, the digital data stream would be fed into the single computer through standard digital video input cards and stored in the computer's main system RAM memory. The data is continuous and so careful memory management through circular buffering in needed to accommodate the data rates without losing data under any conditions. After acquisition, the data may be filtered to enhance the contrast of defects while removing background noise. These filters can be tuned to meet the needs particular applications. Since this is a translucent web, the material is somewhat diffuse, requiring high pass filtering to enhance the defects, but also a smoothing filter to remove noise in the image. Filtering operations are generally computationally expensive for general purpose computers, but by carefully designing the filters, they can be optimized to handle the necessary data rates. Separable filters are common to matrix decomposition and are generally recognized by those skilled in the art. For example, a filter of size 11 by 11 may be separated into two 1 by 11 filters, thereby reducing the number operations from 121 to 22. By choosing this type of filter, an efficiency increase of 550% was realized. Next, the image is efficiently binarized and blobbed as previously described. At this point, anomalies have been isolated as blobs and can be classified by analyzing the blob features (size, shape, position, intensity) using linear or neural network classification techniques generally recognized by those skilled in the art. In this case, defect severity is determined strictly based on size. If defects are greater than 2 mm$^2$, then they are defective, otherwise they fall below the application tolerances and are ignored. Finally, data is displayed to the user through real-time maps and graphs. Data is also stored in real-time archive databases and communicated to the manufacturing process control system to take appropriate action necessary to address the presence of defective material.

For patterned webs, the video signal is expected to contain a repeating pattern such that defects appear as distortions in the pattern. Video processing to identify defective areas involves comparison of the pattern being tested to a template pattern obtained by some other means. The common method of pattern comparison is a direct spatial operation such as subtraction between the pattern under test and the template pattern. However, in practice, this method is not robust for web processes due to normal process variations such as web warping, optical imperfections, edge variations on the pattern, etc. Therefore, after video processing as previously described, this system performs topological blob processing to verify the pattern quality rather than direct image comparison. That is, the number of blob features, their spatial interrelationships, and geometric features are compared against known features to determine if the pattern under test is within specification. With this method, it is much easier to build in tolerances to compensate for normal process variation. Again, data is displayed to the user, stored in archive databases, and communicated to the process control system.

Prior to operation of a patterned web inspection system, a reference image free of defects must be analyzed and critical features extracted. This invention uses a training operation to extract each object (blob) in the reference pattern along with features of the blob such as size, shape, position, topology, etc. In this manner, during run-time, the analysis single computer extracts the blobs in the image under test and compares features of blobs in the runtime list to those in the reference blob list. Through comparison of topological features such as the number of blobs and blob features between the two lists, even subtle pattern defects can be detected. This has the advantage of drastically reducing the amount of data through comparing defect lists rather than full images. Also, it is now possible to compensate for normal process variations by building tolerances into the blob property comparisons. This type of processing has enabled the successful use of single mass market computers for processing the massive amounts of data from patterned web inspection.

For example, in a preferred embodiment for the inspection of flexible circuits in web form, the digital data stream is fed into the single computer through standard digital video input cards and stored in the computer's main system RAM memory. The data is continuous so careful memory management through circular buffering in needed to accommodate the data rates without losing data under any conditions. After acquisition, the data may be filtered, but care should be taken so that the filter does not distort the shape of any of the patterns under examination. Next the video data is binarized and blobbed. Very often, adaptive thresholding is necessary for binarization to compensate for crossweb variations. After the image is blobbed, all analysis operations are performed on the blob list.

Perhaps the most important defect for flexible circuits and PCBs are electrical shorts, opens, lead reductions, and space reductions. First, the blob list generated for open testing is compared to the reference blob count. If the number of run time blobs after filtering spurious noise blobs is more than the number of blobs from training, a circuit open exists. Otherwise, further analysis is required to determine if a trace reduction exists.

Trace reductions represent portions of the circuit in which the metal features are thinned beyond acceptable tolerance. While still electrically conductive, these areas are highly susceptible to failure during operation. In the art, this may be done through the use of morphological processing on the image itself. Unfortunately, because of the massive size of these circuit images (sometimes exceeding 200 megabytes) and the computational cost of morphological processing, custom designed, dedicated electronic hardware has been used to perform these operations. In this invention, the analysis is performed through modification of the blobs rather than the image. First, generate the Y domain segments for each blob from the X domain segments. Next, the X domain and Y domain segments representing blobs are modified. In the case of lead reductions, each segment is reduced symetrically by a predefined number calculated to only pass fully formed traces. Then blobs are reformed as previously described based on the modified segment lists. The number of blobs on the new blob list is compared against a predetermined number, in this particular example, the number of blobs on the training list. If the runtime count is greater than the reference count, then the process of modifying the segment lengths broke the trace and thereby identified a trace reduction.

Next, using a similar mechanism, the part is tested for both shorts and space reductions. The only difference is that the X and Y domain segments are extended rather than reduced. If a short exists, or space reduction exists, then the blob count will be reduced. By operating on the run lengths, computation efficiency is improved by amounts ranging from 500 to 20,0000 times.

If the blob list passes testing described thus far, it still may be defective with traces slightly shortened on one side or with both short and open defects occurring simultaneously. Therefore, the final analysis stage compares position and geometric shape information from each blob in the runtime list against its counterpart in the reference list. Preferable features include, but are not limited to, area, perimeter, moments, or aspect ratios. If any runtime blob is outside acceptable tolerances of its reference counterpart, then the entire part is defective. Otherwise, it has passed all testing for circuitization defects.

One method of maintaining higher accuracy in defect detection on flexible circuits is to use different threshold values for the detection of shorts versus opens. The threshold used for shorts is set to be more sensitive to blob bridging defects and the threshold set for opens is set to be more sensitive to blob breaking defects. For example, for transmitted lighting the traces appear dark. The short threshold may be set at 80% and the open threshold may be set at 20% of the available range.

Another class of defects in this preferred embodiment is stains on metalized features such as wire bond or solder bond pads. These appear as low contrast differences in reflectivity. They are detected by isolating the features using locating techniques as previously described. Once the features have been isolated, the local contrast in that area is measured. If the size of the feature or the contrast across the area is outside specifications, then the part is defective.

Another class of defects in this preferred embodiment is defects in the application or position of covercoat. The covercoat is used for a variety of purposes on flexible circuits including solder dams or dielectric coatings on certain areas of the circuits. Using transflected lighting as previously described, the coating can be isolated from the background and blobs formed representing only the covercoat. Then the blobs can be analyzed in a similar manner to circuitization defects previously described.

Another class of defects in this preferred embodiment is holes or imperfections in the base substrate. For examples, holes in the substrate can cause problems in the products performance. Using transmitted lighting, the product can be imaged such that the holes appear bright on a dark background. Blobs can be formed and defects analyzed similar to uniform web inspection previously described.

Another class of defects in this preferred embodiment is bent leads. Leads are used for bonding the product to external wires or devices. If the lead is bent out of position, proper bonding cannot occur. By using either transmitted light or reflected light, the leads can be isolated from the background and blobbed. Then the number, position, and shape of blobs on the runtime list can be compared against a reference list. The major axis angle has proven to be a particularly important shape parameter for this analysis.

Training

The single computer is typically trained with a standard reference list for comparison against the blob list. The purpose of the product setup or training application is to provide a method for gathering all information needed during the run time inspection process. This includes all binarization and filtering information, defect definitions, pattern matching parameters used for part location on patterned web inspection applications, and product description information. While this application or some variation thereof is required for both uniform and patterned web inspection, it will be illustrated for the preferred embodiment of flexible circuit inspection. Logical adaptations can be made by those skilled in the art to customize for uniform web inspection.

The sequence of operation generally involves: First acquire a defect free image of the web containing at least a full repetition of the pattern; Second, specify the unique features of the pattern and identify the process control areas within the pattern; Third, dictate the specific process control setting for each of the unique inspection regions and defect types; Finally, save and install this information into the database, select this product in the run time application, and run product.

First, with the inspection system set up with proper optics, resolution, lighting, etc., capture an image of the moving web containing at least one full repetition of the repeating pattern. Alternatively, this information can be imported from a CAD (Computer Aided Design) file and translated into the appropriate image format. The image is cropped using conventional image manipulation tools such that the result contains exactly one defect free repetition of the repeating pattern. Thus the image length will be one repetition in the downweb direction and the width will span across the entire web.

The drawing tools are then used to identify a feature of the pattern repeating regularly in the downweb direction, but unique in a localized crossweb area. This feature is identified as the web locator and will be used to track the web position and compensate for any crossweb movement. The downweb distance is defined at a point at which the web locator pattern repeats. Both the pattern and the repeat distance are saved and used in the runtime application to track the web.

The drawing tools are used again to define any discrete "parts" within the repeating pattern. For example, a part may be a single circuit element within a repeating section containing multiple circuits at different orientations. For the part, drawing tools may be used to identify a unique pattern within the part that can be used to locate individual parts within the global pattern. The downweb distance at which the part repeats is defined because there may be multiple parts within a single downweb pattern repetition. Again, the part locator pattern and repeat distance will be used in the runtime inspection to identify individual parts for analysis. The system automatically locates all parts regardless of orientation within the repeating pattern. Optionally, if a downweb repeat pattern contains no discrete parts, then the entire pattern can be treated as a single part. There are several advantages to using the idea of individual parts. In run time, after parts are identified and segmented, all of the analysis is identical. Also, there are often places in the pattern that are of no concern. This method only inspects those areas requiring analysis.

Within the part image, process descriptors needed for inspection are then defined. Process descriptors include: part marker area defining exactly where the defect mark will be placed within a part, display area which defines a critical area of parts for high resolution display to operators, and information used for adaptive binarization.

Regions of interest (ROI's) within the part are then defined. Each ROI identifies an area within the part to which a particular analysis will be applied. For example, with flexible circuits, the whole part may be analyzed for short/open defects, the pad region will be analyzed for stains, and the fine pitch area will be analyzed for lead/space reductions. Each region may be individually identified using graphic tools and the inspection tolerances for each area individually defined. Regions are continuously added until all analyses are defined.

Finally, The file is saved for later revisions, if necessary, and then installed into the inspection system database to be used at run time. Multiple files may be saved for selection during product changes. This permits the operation of the present invention with various products without further intervention.

One of the major difficulties in the inspection of the preferred flexible circuits is that the web can distort due to uneven tensions or variations in the manufacturing process. Therefore, any given portion of the web may be spatially warped from the reference pattern. The defect analysis must be able to compensate for such deformations. The method most often employed is to warp the test image to best match the reference image and then perform a direct spatial comparison, for example, by subtracting the test image from the reference image. Unfortunately, there are difficulties with this approach because it is difficult to correctly warp the image to remove higher order distortions and sometimes the warping cannot compensate for normal process variations. Therefore, it may be necessary to perform "cleanup" processing such as morphological processing after the comparison to remove extraneous noise. Such processing techniques are generally recognized by those skilled in the art.

System Input/Output

The single computer of the present invention generally accepts input from different user controls and signals representing events on the process line. It may accept inputs including web speed, web motion, splice, coating operational, and various synchronization signals. Also, the present invention may provide outputs to various devices upon determination of defects present in the continuously moving web. The single computer may send output commands to devices such as user interface monitors, process control computers, an archiving database, a marking systems or combinations thereof.

Marking systems capable of identifying defective locations or individual parts in a continuously moving web are suitable for use with the present invention. The marking of the defect preferably occurs substantially near the point of occurrence of the defect. Substantially near means that the marking is closely related to the position of the defect in both the cross web and down web direction, and preferably within a tolerance of 5 mm, and most preferably 1 mm.

The purpose of marking defects is to identify defective components or regions so that they may be removed from main production at some later stage. Defect marking subsystems utilize a wide variety of marking techniques, such as, for example, ink or paint deposition (including ink stampers and ink or paint sprayers), lasers tagging, label application (self adhesive labels deposited on or near a defect), hole punching, physical deformation techniques, magnetic pulsing, or combinations thereof. Defect marks may be placed on or near the defect itself, at the edge of the web or at the end of a web roll. Defect marks may also identify defect classification by using different mark colors or shapes. In the case of continuous defects such as streaks on a web, the mark may consist of repetitive small marks as from an ink stamper or a continuous mark as from a paint sprayer.

Conventional marking system are incorporated with use of the present inventive inspection system. For example, ink stamping devices consist of a porous pad loaded with ink and physically placed in contact with the target material to transfer the ink. Ink or paint sprayers utilize a solenoid valve to spray pressurized ink or paint on to the target material. Laser tagging devices incorporate highly concentrated powerful laser beams to physically modify the surface of the target material, typically changing color, burning holes or changing surface texture. Label applicators apply preprinted self-adhesive labels to the target material via a solenoid-activated mechanism. Hole punches physically punch holes in the target material on or near the defect. Many types of punches are possible including conventional punch and die for through punches and kiss-cut punches that do not protrude through the target material and therefore tend to work better on moving webs. Physical deformation of a defective surface can be achieved via devices such as solenoid hammers or knurled wheels that leave distinctive marks on the surface. Magnetic pulses can be applied to a ferrous surface via powerful magnetizing coils such that defects are easily identified later by simple magnetic sensors.

Control of the marking subsystem may be an integral part of the inspection system itself or a semi-autonomous intelligent subsystem (i.e. PLC or dedicated microcomputer) to offload the task from the inspection system. It is the responsibility of the inspection system to identify defects and determine the coordinates both cross web and down web. These defect coordinates are conveyed to the defect marking subsystem which incorporates a delay (time based or distance based) and a synchronization mechanism with the inspection system to accommodate and maintain the physical space between the image sensor and the marker before actuating the marker mechanism.

Device

Figure 7:
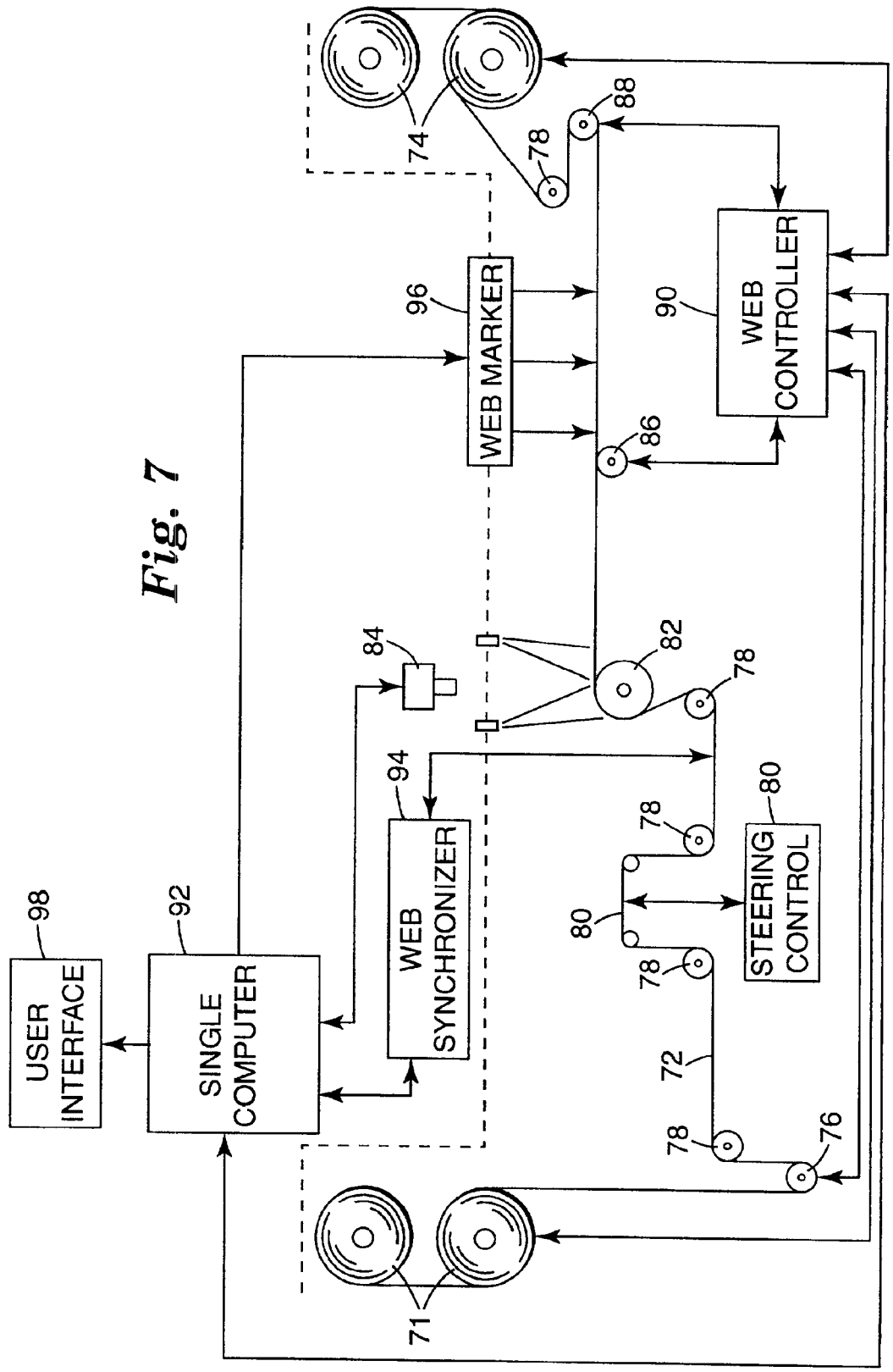
FIG. 7 is a schematic view of a preferred embodiment of a web inspection apparatus.

The device of the present invention generally includes an image acquisition device and a single board computer. The image acquisition device images a sequential portion of a continuously moving web to provide a digital data stream. The single computer forms a blob list from the data stream. The single computer then analyzes the blob list for defects in at least a portion of the continuously moving web. The inspection device of the present invention is generally applied in conventional web production conveying equipment. FIG. 7 depicts one preferred embodiment of the present invention. Web 72 is conveyed from an unwind rollers 71 through the inspection system 70 to a wind up rollers 74. A dancer roller 76 is utilized for tension control. Various idler rolls 78 assist in conveying the web 72. An optional steering mechanism 80 may be provided for guiding the web 72 into the imaging area of the system 70. Inspection idler roll 82 conveys the web under a line scan camera 84. Drive roll 86 is placed downstream of the inspection area in order to minimize the disturbance of the web 72 during imaging due to tension. A tension transducer 88 is conveniently provided to provide feedback to the web controller 90 which send drive signals to the drive roller 86. Image data from the line scan camera 84 is transmitted to the single computer 92 that also receives input from the web synchronizer 94. The single computer 92 forms a blob list and performs the defect analysis. The single computer 92 communicates with a web marking system 96. The web marking system 96 is capable of marking individual defects (not shown) on the web 72. The single computer 92 optionally communicates with the web controller 90 to exchange web 72 product information. The output from the single computer 92 may be reviewed on an optional user interface 98.

Because computational power is at a premium, even with the expedients described above, any efficiencies that can be achieved by reducing computer overhead are preferred. In particular, good results have been achieved using extremely efficient memory management techniques mapping to the computer instruction set and register structure such as specific memory alignment, for example QWORD. The use of SIMD (single instruction multiple data) code has also proved to be preferred. Single computers designed to operate asynchronously and in parallel using multi-threaded techniques are considered preferred.

In an optional embodiment, the method and device of the present invention may utilize multiple imaging systems to provide complete and detailed imaging of a continuously moving web. Multiple imaging devices may be set up parallel across the web to provide an image encompassing the full width of a given substrate. Alternatively, multiple imaging devices may establish in series in various down web locations from one another to adequately inspect for differing types of defects or to monitor for specific types of process related defects at a given point in a web production process.

In another alternative embodiment, two or more inspection systems according to the method and device of the present invention may be established in parallel or in series on a given web. The single computers from each respective system provide data to a central computer. The central computer is then capable of merging or synchronizing the data for improved process control.

The present invention is suitable for inspecting a continuously moving web to identify undesirable occurrences in the web. The method of the present invention may be practiced on any form of web that is suitable for imaging. The method and device are ideally suited to handle massive data rates that are present with complex web materials, such as flexible circuit webs. Additionally, the present invention utilizes imaging devices and a single board computer to handle the massive data rates without custom image processing hardware. The present invention incorporates modular software that adequately supports changes to either specific inspection programs or web materials without requiring additional hardware changes. Further, the single board computer maybe upgraded to capitalize on processing speed enhancements without requiring changes to the software.

What is claimed is:

1. A method of inspecting a continuously moving web, comprising:
    a) imaging a sequential portion of the continuously moving web to provide a digital data stream, wherein the digital data stream corresponding to each sequential portion describes pixels in an X domain corresponding to their position accross the web,
    b) binarizing said digital data stream,
    c) forming a blob list from the data stream by;
        c1) determining collections of pixels connected to each other in the X domain so as to define segments, and
        c2) resolving line to line whether connections exist between segments in a Y domain corresponding to the direction of web movement; wherein the determining step and the resolving step are accomplished in a single iteration, and
    d) analyzing blobs on the blob list to identify defects, wherein c) and d) occur in a single computer.

2. A method according to claim 1, further comprises saving in turn a list of the segments in each sequential line as a comparison list, and wherein
    the resolving comprises comparing the segment list for the current line with the comparison list.

3. A method according to claim 1, wherein a filter is applied to the digital data stream in the single computer prior to forming the blob list.

4. A method according to claim 1, further comprising communicating between the single computer and a process control system.

5. A method according to claim 1, further comprising marking identified defects on the continuously moving web.

6. A method according to claim 5, wherein said marking occurs through ink deposition, paint deposition, laser tagging, label application, hole punching, physical deformation, magnetic pulsing or combinations thereof.

7. A method according to claim 5, wherein said marking occurs substantially near the point of occurrence of the defect.

8. A method according to claim 1, wherein said web is selected from metals, paper, polymeric films, wovens, nonwovens, glass or combinations thereof.

9. A method according to claim 8, wherein one or more coatings or one or more patterns are applied to said web.

10. A method according to claim 9, wherein said continuously moving web is a flexible circuit web.

11. A method according to claim 1, wherein said imaging occurs through reflected light transmitted light or transflected light.

12. A method according to claim 1, wherein multiple imaging sources are utilized.

13. A method according to claim 1, wherein said binarizing includes adaptive thresholding or multiple value thresholding.

14. A method according to claim 1, wherein said data stream is at least 10 mega-pixels/second.

15. A method according to claim 1, further comprising classifying defects into specific categories.

16. A method comprising:
    a) imaging a sequential portion of the continuously moving web to provide a digital data stream,
    b) forming a blob list from the data stream, and
    c) analyzing blobs on the blob list to identify defects, wherein b) and c) occur in a single computer,
    wherein the web is a patterned web, and further comprising binarizing the digital data stream prior to forming the blob list, the binarizing comprising:
    identifying at least one sequential portion having substantially the entire range of optical properties characteristic of the web;
    identifying the pixel values corresponding to local maxima and minima;

defining a range bounded by the lowest value among the pixel values identified as local maxima and the highest value among the pixel values identified as local minima;

calculating a threshold value within the range; and comparing at least a portion of the digital data stream to the threshold value.

17. A method of inspecting continuously moving articles on a web, comprising analyzing blobs formed from a continuous digital data stream of at least 10 mega-pixels/second imaged from at least a portion of a continuously moving article to identify defects on the articles, wherein the blobs are formed and analyzed in a single computer, and further wherein the digital data stream describes pixels in an X domain corresponding to their position accross the web, the method further comprising:

a) binarizing said digital data stream; and b) forming the blobs from the digital data stream by determining collections of pixels connected to each other in the X domain so as to define segments, and resolving line to line whether connections exist between segments in a Y domain corresponding to the direction of web movement, wherein the determining and the resolving are accomplished in a single iteration.

18. A method for inspecting continuously moving webs having a repeating pattern, the method comprising:

a) imaging sequential portions of the continuously moving web to provide a digital data stream, wherein the digital data stream corresponding to each sequential portion describes pixels in an X domain corresponding to their position accross the web, b) identifying instances of the repeating pattern, c) forming a blob list representative of each instance of the repeating pattern from the data stream, wherein the blob list includes information on the lengths of collections of pixels connected to each other in the X domain, and d) analyzing blobs on the blob list to identify defects, wherein c) and d) occur in a single computer and the analyzing step comprises:

caculating information on the lengths of colletions of pixels connected to each other in a Y domain corresponding to the direction of web movement;

modifying the lengths of the collections of pixels in at least one of the X domain, the Y domain or both domains, by a first predetermined number;

preparing a new blob list based on the modified lengths; and comparing the number of blobs on the new blob list against a second predetermined number.

19. A method according to 18, wherein the number of blobs on the blob list for each instance of the repeating pattern is compared against a predetermined number.

20. A method according to 18, wherein positional and geometric properties of each blob is compared against a corresponding blob in a reference blob list.

21. A method according to 18, wherein said imaging occurs through reflected light, transmitted light or transflected light.

22. A method according to claim 18, wherein the data stream is utilized to find individual patterns on said web without external synchronization.

23. A method according to claim 18, further comprising binarizing of said digital data stream prior to forming said blob list.

24. A method according to claim 23, wherein said binarizing occurs using adaptive thresholding or multiple value thresholding.

25. A method according to claim 18, wherein said continuously moving web is a flexible circuit web.

26. A method according to claim 25, wherein said defects include one or more of shorts, opens, lead reductions, space reductions, substrate defects, pattern misregistration, bent leads, covercoat defects, lamination defects, stains, or debris.

27. A method according to claim 18, further comprising marking one or more defects on said continuously moving web.

28. A method according to claim 18, wherein said marking occurs substantially near the point of occurrence of the defect.

29. A method according to claim 18, wherein said computer communicates with a process control system that controlls said continuously moving web.

30. A method according to claim 18, wherein said imaging device is spatially synchronized to the continuously moving web.

31. A method according to claim 18, wherein multiple imaging sources are utilized.

32. A method according to claim 18, further comprising classifying defects into specific categories.

33. A device for inspecting a continuously moving web, comprising (a) An imaging device for sequentially imaging a portion of a continuously moving web to provide a digital data stream; and (b) A single computer capable of forming a blob list from the data stream and analyzing the blob list in order to identify defects in at least a portion of said continuously moving web, wherein the digital data stream corresponding to each sequential portion describes pixels in an X domain corresponding to their position across the web, and wherein the blob list includes information on the lengths of collections of pixels connected to each other in the X domain, and further wherein the computer analyzes the blob list by:

calculating information on the lengths of collections of pixels connected to each other in a Y domain corresponding to the direction of web movement;

modifying the lengths of the collecions of pixels in at least one of the X domain, the Y domain, or both domains by a first predetermined number;

preparing a new blob list based on the modified lengths; and comparing the number of blobs on the new blob list against a second predetermined number.

34. A device according to claim 33, further comprising a process control system in communication with the single computer.

35. A device according to claim 33, further comprising a marking system for marking identified defects on the continuously moving web.

36. A device according to claim 33, wherein said imaging device is a line scan camera.

37. A device according to claim 33, wherein said imaging device utilizes optical assemblies which utilize reflected light, transmitted light or transflected light.

38. A device according to claim 33, wherein multiple imaging devices are utilized.

39. A device for inspecting flexible circuits, comprising (a) An imaging device for sequentially imaging a portion of a continuously moving flexible circuit web to provide a digital data stream; and (b) A single computer capable of forming a blob list from the data stream and analyzing the blob list in order to identify defects in at least a portion of said continuously moving flexible circuit web, wherein the digital data stream corresponding to each sequential portion describes pixels in an X domain corresponding to their position accross the web, and wherein the blob list includes information on the lengths of collections of pixels connected to each other in the X domain, and further wherein the computer analyzes the blob list by:

calculating information on the lengths of collections of pixels connected to each other in a Y domain corresponding to the direction of web movement;

modifying the lengths of the collections of pixels in at least one of the X domain, the Y domain, or both domains, by a first predetermined number;

preparing a new blob list based on the modified lengths; and comparing the number of blobs on the new blob list against a second predetermined number.

40. A device according to claim 39, further comprising a process control system in communication with the single computer.

41. A device according to claim 39, further comprising a marking system for marking identified defects on the continuously moving web.

42. A device according to claim 39, wherein said imaging device is a line scan camera.

43. A device according to claim 39, wherein said imaging device utilizes optical assemblies which utilize reflected light, transmitted light or transflected light.

44. A device according to claim 39, wherein multiple imaging devices are utilized.

45. A method of inspecting a flexible circuit web, comprising analyzing blobs formed from a continuous digital data stream of at least 10 mega-pixels/second imaged from at least a portion of a flexible circuit web to identify defects on the flexible circuit web, wherein the blobs are formed and analyzed in a single computer, and further wherein the digital data stream describes pixels in an X domain corresponding to their position accross the web, the method further comprising:

a) binarizing said digital data stream; and b) forming the blobs from the digital data stream by determining collections of pixels connected to each other in the X domain so as to define segments, and resolving line to line whether connections exist between segments in a Y domain corresponding to the direction of web movement, wherein the determining and the resolving are accomplished in a single iteration.

46. A method comprising:

imaging a continuously moving web to provide a digital data stream, wherein the digital data stream describes pixels in an X domain corresponding to their position across the web;

forming a data structure from the data stream, wherein the data structure includes a set of objects, each object describing a set of pixels within the digital data stream that each have binary values that satisfy a connection threshold; and analyzing the objects of the data structure to identify defects within the web;

wherein forming the data structure comprises;

determining sets of pixels that satisfy a pixel connection threshold in the X domain so as to define segments;

resolving line to line whether connections exist between segments in a Y domain corresponding to the direction of web movement; and storing information within one of the objects of the data structure to describe the sets of pixels upon resolving the connections.

47. A method according to claim 46, wherein the objects store data that describe at least a start position and an end position for the corresponding set of connected pixels within the digital data stream.

* * * * *

UNITED STATES PATENT AND TRADEMARK OFFICE
CERTIFICATE OF CORRECTION

| | |
|---|---|
| PATENT NO. | : 6,950,547 B2 |
| APPLICATION NO. | : 09/781372 |
| DATED | : September 27, 2005 |
| INVENTOR(S) | : Floeder, Steven P. |

It is certified that error appears in the above-identified patent and that said Letters Patent is hereby corrected as shown below:

<u>Title page,</u>
Item [75], Inventors, delete "Xi Yu" and insert -- Xin Yu --.

<u>Column 2,</u>
Line 53, delete "eg" and insert -- e.g. --.

<u>Column 3,</u>
Line 17, delete "transfected" and insert -- transflected --.

<u>Column 4,</u>
Line 61, delete "a" and insert -- an --.

<u>Column 6,</u>
Line 37, after "interest" insert -- . --.

<u>Column 18,</u>
Line 3, delete "across" and insert -- across --;
Line 5, after "by" delete ";" and insert -- : --;
Line 30, delete "hole" and insert -- hold --;
Line 40, after "reflected light" insert -- , -- .

<u>Column 19,</u>
Lines 15 and 30, delete "accross" and insert -- across --;
Line 40, delete "caculating" and insert -- calculating --;
delete "collections" and insert -- collections --;
Line 44, after "Y domain" insert -- , --;
Lines 50, 53 and 56, delete "18" and insert -- claim 18 --;
Line 54, after "blob" delete "is" and insert -- are --.

<u>Column 20,</u>
Line 11, delete "claim 18" and insert -- claim 27 --;
Line 16, delete "controlls" and insert -- controls --;
Line 42, delete "collecions" and insert -- collections --;
Line 44, after "domains" insert -- , --.

UNITED STATES PATENT AND TRADEMARK OFFICE
CERTIFICATE OF CORRECTION

PATENT NO. : 6,950,547 B2
APPLICATION NO. : 09/781372
DATED : September 27, 2005
INVENTOR(S) : Floeder, Steven P.

It is certified that error appears in the above-identified patent and that said Letters Patent is hereby corrected as shown below:

Column 21,
Line 5, delete "accross" and insert -- across --.

Column 22,
Line 1, delete "accross" and insert -- across --;
Line 23, after "web" delete ";" and insert -- , --.

Signed and Sealed this

Eleventh Day of July, 2006

JON W. DUDAS
*Director of the United States Patent and Trademark Office*